US007867215B2

(12) United States Patent
Åkerlund et al.

(10) Patent No.: US 7,867,215 B2
(45) Date of Patent: Jan. 11, 2011

(54) METHOD AND DEVICE FOR FLUID TRANSFER IN AN INFUSION SYSTEM

(75) Inventors: Roger Åkerlund, Göteborg (SE); Kjell Andreasson, Västra Frölunda (SE)

(73) Assignee: Carmel Pharma AB, Gothenburg (SE)

( * ) Notice: Subject to any disclaimer, the term of this patent is extended or adjusted under 35 U.S.C. 154(b) by 1145 days.

(21) Appl. No.: 10/063,386

(22) Filed: Apr. 17, 2002

(65) Prior Publication Data

US 2003/0199847 A1 Oct. 23, 2003

(51) Int. Cl.
*A61B 19/00* (2006.01)

(52) U.S. Cl. ........................ 604/413; 604/411; 604/414

(58) Field of Classification Search ................. 604/403, 604/411–416, 905; 206/222, 265
See application file for complete search history.

(56) References Cited

U.S. PATENT DOCUMENTS

| | | | |
|---|---|---|---|
| 1,844,342 | A | 2/1932 | Berman |
| 2,010,417 | A | 8/1935 | Schwab |
| 2,697,438 | A | 12/1954 | Hickey |
| 2,717,599 | A | 9/1955 | Huber |
| 3,064,651 | A | 11/1962 | Henderson |
| 3,071,135 | A | 1/1963 | Baldwin et al. |
| 3,308,822 | A | 3/1967 | DeLuca |
| 3,316,908 | A | 5/1967 | Burke |
| 3,390,677 | A | 7/1968 | Razimbaud |
| 3,448,740 | A | 6/1969 | Figge |
| 3,542,240 | A | 11/1970 | Solowey |
| 3,783,895 | A | 1/1974 | Weichselbaum |
| 3,788,320 | A | 1/1974 | Dye |
| 3,822,700 | A | 7/1974 | Pennington |
| 3,938,520 | A | 2/1976 | Scislowicz et al. |
| 3,976,073 | A | 8/1976 | Quick et al. |
| 4,096,860 | A | 6/1978 | McLaughlin |
| 4,296,786 | A | 10/1981 | Brignola |
| 4,490,139 | A | 12/1984 | Huizenga et al. |

(Continued)

FOREIGN PATENT DOCUMENTS

AU 200112863 B2 5/2001

(Continued)

OTHER PUBLICATIONS

Taiwan Search Report for Taiwan Patent Application 092106323, dated Mar. 21, 2003.

(Continued)

*Primary Examiner*—Leslie R Deak
(74) *Attorney, Agent, or Firm*—Fish & Richardson P.C.

(57) ABSTRACT

A fluid transfer device for use in an infusion system having a first end and a second end for coupling to an injection port of the infusion system. The device further includes at least a first member, a hollow needle attached to the first member, and a second member telescopically displaceable in relation to the first member, allowing the hollow needle to penetrate a flexible barrier member sealing the injection port thereby creating a fluid passage into the infusion system. The first end has a connecting portion for attachment to a drug bottle containing a fixed dose of a medical substance, and the second end has a flexible membrane able to be pressed against the flexible barrier member with a pressure sufficient to create a double-membrane sealing around the hollow needle.

36 Claims, 8 Drawing Sheets

U.S. PATENT DOCUMENTS

| | | | | |
|---|---|---|---|---|
| 4,516,967 | A | 5/1985 | Kopfer | |
| 4,564,054 | A | 1/1986 | Gustavsson | |
| 4,573,967 | A | 3/1986 | Hargrove et al. | |
| 4,576,211 | A | 3/1986 | Valentini et al. | |
| 4,581,016 | A | 4/1986 | Gettig | |
| 4,582,223 | A | 4/1986 | Kobe | |
| 4,588,403 | A | 5/1986 | Weiss et al. | |
| 4,600,040 | A | 7/1986 | Naslund | |
| 4,623,343 | A | 11/1986 | Thompson | |
| 4,629,455 | A | 12/1986 | Kanno | |
| 4,632,673 | A | 12/1986 | Tiitola et al. | |
| 4,636,204 | A | 1/1987 | Christopherson et al. | |
| 4,673,400 | A | 6/1987 | Martin | |
| 4,673,404 | A | 6/1987 | Gustavsson | |
| 4,737,150 | A | 4/1988 | Baeumle et al. | |
| 4,752,287 | A | 6/1988 | Kurtz et al. | |
| 4,768,568 | A | 9/1988 | Fournier et al. | |
| 4,792,329 | A | 12/1988 | Schreuder | |
| 4,804,015 | A | 2/1989 | Albinsson | |
| 4,822,340 | A | 4/1989 | Kamstra | |
| 4,826,492 | A | 5/1989 | Magasi | |
| 4,834,717 | A | 5/1989 | Haber et al. | |
| 4,842,585 | A | 6/1989 | Witt | |
| 4,850,978 | A | 7/1989 | Dudar et al. | |
| 4,864,717 | A | 9/1989 | Baus, Jr. | |
| 4,872,494 | A | 10/1989 | Coccia | |
| 4,878,897 | A | 11/1989 | Katzin | |
| 4,889,529 | A | 12/1989 | Haindl | |
| 4,898,209 | A | 2/1990 | Zbed | |
| 4,909,290 | A | 3/1990 | Coccia | |
| 4,932,937 | A | 6/1990 | Gustavsson et al. | |
| 4,944,736 | A | 7/1990 | Holtz | |
| 4,964,855 | A | 10/1990 | Todd et al. | |
| 4,982,769 | A | 1/1991 | Fournier et al. | |
| 4,994,048 | A | 2/1991 | Metzger | |
| 4,997,083 | A | 3/1991 | Loretti et al. | |
| 5,017,186 | A | 5/1991 | Arnold | |
| 5,041,105 | A | 8/1991 | D'Alo et al. | |
| 5,061,264 | A | 10/1991 | Scarrow | |
| 5,071,413 | A | 12/1991 | Utterberg | |
| 5,122,116 | A | 6/1992 | Kriesel et al. | |
| 5,122,123 | A | 6/1992 | Vaillancourt | |
| 5,137,524 | A | 8/1992 | Lynn et al. | |
| 5,158,554 | A | 10/1992 | Jepson et al. | |
| 5,176,673 | A | 1/1993 | Marrucchi | |
| 5,199,947 | A | 4/1993 | Lopez et al. | |
| 5,201,725 | A | 4/1993 | Kling | |
| 5,207,658 | A | 5/1993 | Rosen et al. | |
| 5,232,109 | A | 8/1993 | Tirrell et al. | |
| 5,254,097 | A | 10/1993 | Schock et al. | |
| 5,279,576 | A | 1/1994 | Loo et al. | |
| 5,279,583 | A | 1/1994 | Shober, Jr. et al. | |
| 5,279,605 | A | 1/1994 | Karrasch et al. | |
| 5,308,347 | A | 5/1994 | Sunago et al. | |
| 5,312,366 | A | 5/1994 | Vaillancourt | |
| 5,328,480 | A | 7/1994 | Melker et al. | |
| 5,334,163 | A | 8/1994 | Sinnett | |
| 5,356,406 | A | 10/1994 | Schraga | |
| 5,385,545 | A | 1/1995 | Kriesel et al. | |
| 5,385,547 | A | 1/1995 | Wong et al. | |
| 5,389,085 | A | 2/1995 | D'Alessio et al. | |
| 5,405,326 | A | 4/1995 | Haber et al. | |
| 5,445,630 | A | 8/1995 | Richmond | |
| 5,447,501 | A | 9/1995 | Karlsson et al. | |
| 5,456,675 | A | 10/1995 | Wolbring et al. | |
| 5,470,522 | A | 11/1995 | Thome et al. | |
| 5,478,328 | A | 12/1995 | Silverman et al. | |
| 5,478,337 | A * | 12/1995 | Okamoto et al. | 604/413 |
| 5,492,531 | A | 2/1996 | Post et al. | |
| 5,514,117 | A | 5/1996 | Lynn | |
| 5,515,871 | A | 5/1996 | Bittner et al. | |
| 5,536,259 | A | 7/1996 | Utterberg | |
| 5,575,780 | A | 11/1996 | Saito | |
| 5,593,028 | A | 1/1997 | Haber et al. | |
| 5,613,954 | A | 3/1997 | Nelson et al. | |
| 5,632,735 | A | 5/1997 | Wyatt et al. | |
| 5,647,845 | A | 7/1997 | Haber et al. | |
| 5,685,866 | A | 11/1997 | Lopez | |
| 5,752,942 | A | 5/1998 | Doyle et al. | |
| 5,766,147 | A | 6/1998 | Sancoff et al. | |
| 5,766,211 | A | 6/1998 | Wood et al. | |
| 5,782,872 | A | 7/1998 | Muller | |
| 5,795,336 | A | 8/1998 | Romano et al. | |
| 5,817,083 | A | 10/1998 | Shemesh et al. | |
| 5,820,609 | A | 10/1998 | Saito | |
| 5,827,262 | A | 10/1998 | Neftel et al. | |
| 5,837,262 | A | 11/1998 | Golubev et al. | |
| 5,879,345 | A | 3/1999 | Aneas | |
| 5,897,526 | A | 4/1999 | Vaillancourt | |
| 5,934,510 | A | 8/1999 | Anderson | |
| 5,984,899 | A | 11/1999 | D'Alessio et al. | |
| 6,063,068 | A * | 5/2000 | Fowles et al. | 604/414 |
| 6,070,623 | A | 6/2000 | Aneas | |
| 6,071,270 | A | 6/2000 | Fowles et al. | |
| 6,090,091 | A * | 7/2000 | Fowles et al. | 604/403 |
| 6,113,068 | A | 9/2000 | Ryan | |
| 6,113,583 | A | 9/2000 | Fowles et al. | |
| 6,142,446 | A | 11/2000 | Leinsing | |
| 6,146,362 | A | 11/2000 | Turnbull et al. | |
| 6,209,738 | B1 | 4/2001 | Jansen et al. | |
| 6,221,065 | B1 | 4/2001 | Davis | |
| 6,245,056 | B1 | 6/2001 | Walker et al. | |
| 6,253,804 | B1 | 7/2001 | Safabash | |
| 6,258,078 | B1 | 7/2001 | Thilly | |
| 6,387,074 | B1 | 5/2002 | Horppu et al. | |
| 6,453,956 | B2 | 9/2002 | Safabash | |
| 6,471,674 | B1 | 10/2002 | Emig et al. | |
| 6,517,523 | B1 | 2/2003 | Kaneko et al. | |
| 6,537,263 | B1 | 3/2003 | Aneas | |
| 6,571,837 | B2 | 6/2003 | Jansen et al. | |
| 6,591,876 | B2 | 7/2003 | Safabash | |
| 6,644,367 | B1 | 11/2003 | Savage et al. | |
| 6,685,692 | B2 * | 2/2004 | Fathallah | 604/411 |
| 6,715,520 | B2 | 4/2004 | Andreasson et al. | |
| 6,786,244 | B1 | 9/2004 | Jones | |
| 6,960,194 | B2 | 11/2005 | Hommann et al. | |
| 7,080,672 | B2 | 7/2006 | Fournier et al. | |
| 7,297,140 | B2 * | 11/2007 | Orlu et al. | 604/411 |
| 7,703,486 | B2 | 4/2010 | Costanzo | |
| 7,744,581 | B2 | 6/2010 | Wallen et al. | |
| 2001/0021825 | A1 | 9/2001 | Becker et al. | |
| 2001/0025671 | A1 | 10/2001 | Safabash | |
| 2002/0002352 | A1 | 1/2002 | Becker et al. | |
| 2002/0082586 | A1 | 6/2002 | Finley et al. | |
| 2002/0177819 | A1 | 11/2002 | Barker et al. | |
| 2003/0010717 | A1 | 1/2003 | Brugger et al. | |
| 2003/0070726 | A1 | 4/2003 | Andreasson et al. | |
| 2003/0106610 | A1 | 6/2003 | Roos et al. | |
| 2003/0107628 | A1 | 6/2003 | Fowles et al. | |
| 2003/0199846 | A1 | 10/2003 | Fowles et al. | |
| 2003/0233083 | A1 | 12/2003 | Houwaert et al. | |
| 2004/0116858 | A1 | 6/2004 | Heinz et al. | |
| 2004/0199139 | A1 | 10/2004 | Fowles et al. | |
| 2004/0215147 | A1 | 10/2004 | Wessman et al. | |
| 2005/0215977 | A1 | 9/2005 | Uschold | |
| 2006/0025747 | A1 | 2/2006 | Sullivan et al. | |
| 2006/0106360 | A1 | 5/2006 | Wong | |
| 2006/0111667 | A1 | 5/2006 | Matsuura et al. | |
| 2006/0157984 | A1 | 7/2006 | Rome et al. | |
| 2006/0186045 | A1 | 8/2006 | Jensen et al. | |
| 2007/0021725 | A1 | 1/2007 | Villette | |
| 2007/0060841 | A1 | 3/2007 | Henshaw | |
| 2007/0106244 | A1 | 5/2007 | Mosler et al. | |
| 2007/0179441 | A1 | 8/2007 | Chevallier | |

| | | | |
|---|---|---|---|
| 2007/0270759 A1 | 11/2007 | Pessin | |
| 2008/0045919 A1 | 2/2008 | Jakob et al. | |
| 2008/0103453 A1 | 5/2008 | Liversidge | |
| 2008/0103485 A1 | 5/2008 | Kruger | |
| 2008/0172039 A1 | 7/2008 | Raines | |
| 2008/0223484 A1 | 9/2008 | Horppu | |
| 2008/0287920 A1 | 11/2008 | Fangrow et al. | |
| 2008/0312634 A1 | 12/2008 | Helmerson et al. | |
| 2009/0254042 A1 | 10/2009 | Gratwohl et al. | |

FOREIGN PATENT DOCUMENTS

| | | |
|---|---|---|
| DE | 2005519 | 10/1979 |
| EP | 0255025 | 2/1988 |
| EP | 0259582 | 3/1988 |
| EP | 0285424 | 10/1988 |
| EP | 0311787 | 4/1989 |
| EP | 0376629 | 7/1990 |
| EP | 0 803 267 | 10/1997 |
| EP | 0819442 | 1/1998 |
| EP | 0995453 | 4/2000 |
| EP | 1060730 | 12/2000 |
| EP | 1484073 | 12/2004 |
| EP | 1731128 | 12/2006 |
| FR | 2757405 | 6/1998 |
| FR | 2780878 | 1/2000 |
| GB | 1579065 | 11/1980 |
| JP | 49-12690 | 5/1972 |
| JP | 288664 | 7/1990 |
| JP | 3030963 | 8/1996 |
| JP | 2000167022 | 6/2000 |
| JP | 2001505092 | 4/2001 |
| JP | 2001293085 | 10/2001 |
| TW | 0482670 B | 4/2002 |
| WO | 8404673 | 12/1984 |
| WO | WO 84/04672 | 12/1984 |
| WO | WO 90/03536 | 4/1990 |
| WO | WO 98/19724 | 5/1998 |
| WO | WO 99/27886 | 6/1999 |
| WO | WO 99/62578 | 12/1999 |
| WO | WO 00/15292 | 3/2000 |
| WO | WO 00/35517 | 6/2000 |
| WO | WO 01/80928 | 11/2001 |
| WO | WO 02/02048 | 1/2002 |
| WO | WO 02/11794 | 2/2002 |
| WO | 02/064077 | 8/2002 |
| WO | WO 02/076540 | 10/2002 |
| WO | WO 2005/074860 | 8/2005 |
| WO | WO 2006/082350 | 8/2006 |
| WO | WO 2006/083333 | 8/2006 |
| WO | WO 2008/115102 | 9/2008 |
| WO | WO 2006/138184 | 12/2009 |

OTHER PUBLICATIONS

Japanese Application No. 2003-583539; Official Action dated May 1, 2009 (3 pages).
Japan Application No. 2003-577789, Official Action dated Feb. 24, 2009 (4 pages).
International Search Report, PCT/EP2008/067535 dated Oct. 13, 2009 (3 pages).
International Search Report, PCT/EP2008/067522 dated Aug. 12, 2009 (2 pages).

* cited by examiner

METHOD AND DEVICE FOR FLUID TRANSFER IN AN INFUSION SYSTEM

BACKGROUND OF INVENTION

1. Technical Field

The present invention relates to a fluid transfer device for use in an infusion system. The device includes a first end, a second end opposite the first end, the second end being designed and arranged for coupling to an injection port of the infusion system. The fluid transfer device further includes at least a first member, a hollow needle attached to the first member, and a second member telescopically displaceable in relation to the first member whereby the hollow needle is able to penetrate a flexible barrier member sealing the injection port in order to create a fluid passage from the first end via the injection port into the infusion system. The present invention also relates to a drug bottle for use with the fluid transfer device, and a method for fluid transfer which utilizes the fluid transfer device.

2. Background Information

A serious problem in connection with drug preparation, drug administration and other similar handling is the risk that medical and pharmacological staff are exposed to drugs or solvents Which might escape into the ambient air. This problem is particularly serious when cytotoxins, antiviral drugs, antibiotics and radiopharmaceuticals are concerned.

For this reason, there has been a need of safer systems for handling and administrating drugs and other medical substances.

Accordingly, U.S. Pat. No. 4,564,054 to Gustavsson ("the '054 patent") discloses a fluid transfer device for transferring a substance from one vessel to another vessel while avoiding leakage of liquid and gas contaminants. The transfer device includes a first member designed as a hollow sleeve and having a piercing member provided with a passageway. The piercing member is attached to the first member, which has a first barrier member at one end opposite the tip of the piercing member. Thereby, the piercing member can be passed and retracted through the first barrier member which seals one end of the first member.

The fluid transfer device further includes a second member attached to or attachable to one of the vessels or to a means for communicating therewith. The second member has a second barrier member, and mating connection means positioned or arranged on the first and second members for providing a releasable locking of the members with respect to each other. The barrier members are liquid and gas-proof sealing members which seal tightly after penetration and retraction of the piercing member and prevent leakage of liquid as well as gas contaminants. In the connected position of the first and second members, the baffler members are located in such a way with respect to each other that the piercing member can be passed there through.

According to the '054 patent, the above-mentioned piercing member is a needle arranged for puncturing the first and the second baffler members, wherein the end opposite the one end of the first member has means for sealingly receiving or being permanently attached to an injection syringe or the like for withdrawing and/or adding substance to the vessel attached to the second member. When attached to the first member, the injection syringe or the like communicates with the passageway of the needle so that, in the retracted position, the needle is hermetically enclosed in the first member having the injection syringe or the like connected thereto.

International Patent Publication No. WO 99/27886 to Fowles et al. ("the '886 publication") discloses a connector device intended for establishing fluid communication between a first container and a second container. The connector device includes a first sleeve member having a first and a second end. The first sleeve member has a first attaching member at the first end, which is adapted to attach to the first container.

The connector device further includes a second sleeve member having a first end and a second end. Thereby, the second sleeve member is associated with the first sleeve member and movable with respect thereto from an inactivated position to an activated position. The second sleeve member has a second attaching member at the second end adapted to attach the second sleeve member to the second container.

According to the '886 publication, the connector device further includes a first and second piercing member projecting from one of the first and second sleeve members. These piercing members are adapted for providing a fluid flow path from the first container to the second container. The connector device further includes means for independently hermetically sealing the first and second members.

Furthermore, U.S. Pat. No. 6,258,078 B1 discloses a luer connector that facilitates connection of a hypodermic syringe to the vial. The connector includes a luer connectable to a syringe and which extends to a sharpened end capable of being driven through a penetrable vial closure thereby puncturing the closure, a luer support mountable on a vial and which initially supports the luer in a first position in which the sharpened end of the conduit is pointed towards the closure, and a luer driver such that movement of the driver relative to the support causes the luer to be driven so that the sharpened end punctures the closure and enters the vial.

When performing infusion, it is often necessary to inject a drug or other medical substance into the infusion fluid inside an infusion bag or other infusion fluid container. This is often done by means of penetrating a septum or other fluid barrier of an injection port on the infusion bag or on the infusion fluid line with a needle of a syringe filled with the medical fluid in question.

However, it has been found that the use of a regular syringe or other device according to prior art, when injecting hazardous substances such as cytotoxins into an infusion bag or infusion fluid line, might cause pollution of the working environment because of leakage, something which of course is unacceptable. For this reason, there is a need of an improved device which eliminates the risk that potentially health-hazardous substances escape into the ambient air or working environment when injecting a drug or another medical substance into an infusion system, and which device safely can be disconnected from the infusion system after having performed the injection.

SUMMARY OF INVENTION

Accordingly, the present invention provides a simple, reliable and safe fluid transfer device for use when injecting a medical substance into an infusion system. The device substantially eliminates the risk of hazardous substances escaping into the environment.

This is achieved by a fluid transfer device having a first end and a second end opposite the first end. The second end is designed and arranged for coupling to an injection port of the infusion system. The fluid transfer device includes at least a first member, a hollow needle attached to the first member, and a second member which is telescopically displaceable in relation to the first member in a way that the hollow needle is able to penetrate a flexible barrier member sealing the injection port, thereby creating a fluid passage from the first end via the injection port into the infusion system. The first end includes a connecting portion for attachment to a drug bottle containing a fixed dose of a medical substance. The second end includes a flexible membrane for pressing against the flexible barrier member of the injection port with a pressure sufficient to create a double-membrane sealing around the hollow needle when creating the fluid passage into the infusion system.

The present invention also provides a drug bottle for use with the fluid transfer device according to the invention. This is achieved by a drug bottle containing a fixed dose of a medical substance, and which is intended for attaching to the fluid transfer device according to the invention.

The present invention further provides a method for fluid transfer in an infusion system which utilizes the fluid transfer device according to the invention. The method includes using a fluid transfer device to inject a medical substance into the infusion system via an injection port sealed by a flexible baffler member. The fluid transfer device includes at least a first member, a hollow needle attached to the first member, and a second member telescopically displaceable in relation to the first member. The method includes providing the fluid transfer device having a first end, and a second, opposite end exhibiting a flexible membrane, providing a drug bottle containing a fixed dose of the medical substance, attaching the first end to the drug bottle, and coupling the second end to the injection port while pressing the flexible membrane against the flexible barrier member with a pressure sufficient for creating a double-membrane sealing. The method further includes creating a fluid passage from the first end to the infusion system by telescopically displacing the first end in a direction towards the second end in order to get the hollow needle to penetrate the flexible membrane and the flexible barrier member while being surrounded by the double-membrane sealing, and transferring the fixed dose from the drug battle into the infusion system by creating and subsequently releasing a positive pressure inside the drug bottle.

Further objects of the present invention will become evident from the following description and the attached claims.

BRIEF DESCRIPTION OF DRAWINGS

In the following, the present invention will be described in greater detail with reference to the attached drawings, in which.

DETAILED DESCRIPTION

Figure 1:
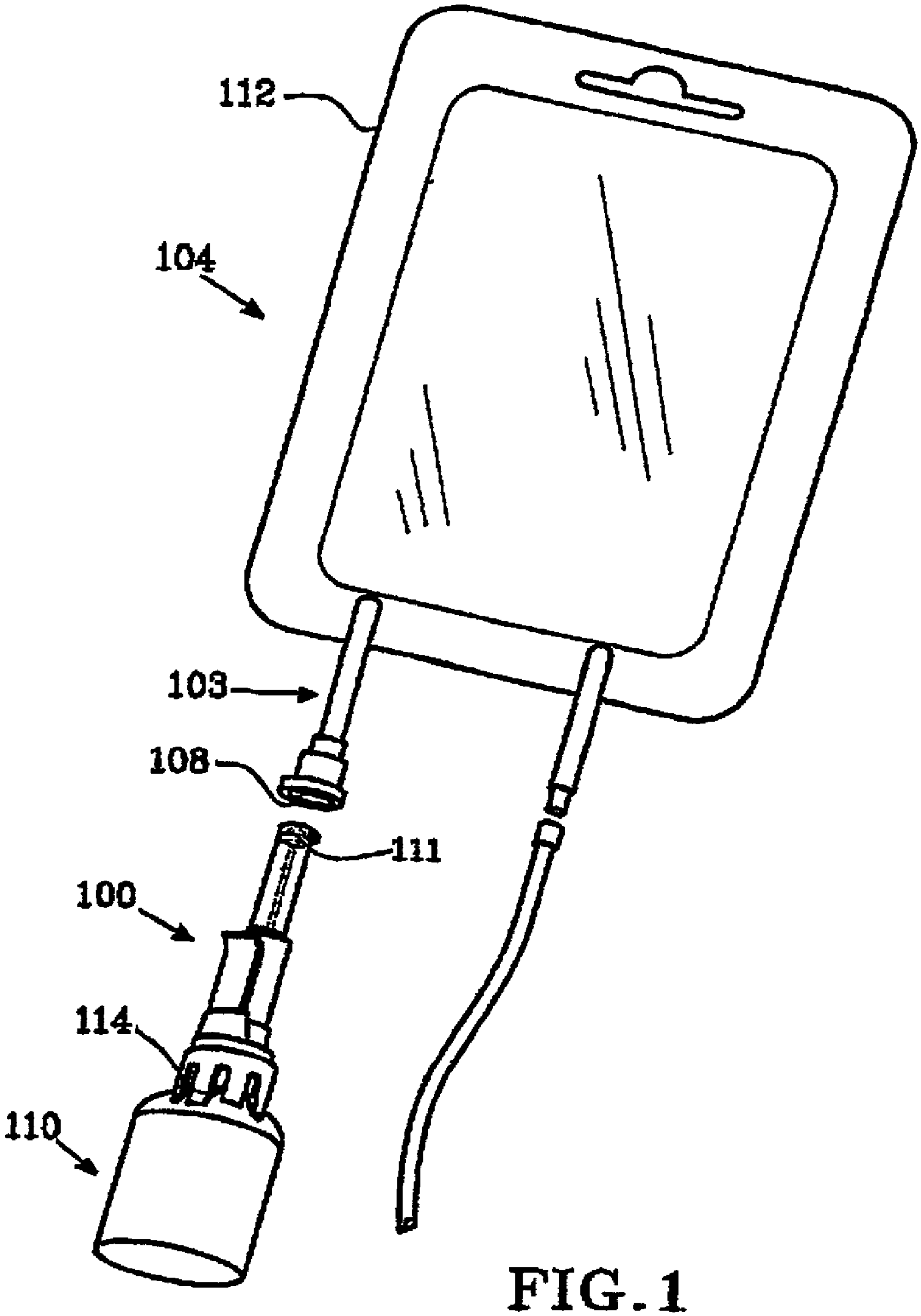
FIG. 1 is a schematic illustration of a portion of an infusion system in which a fluid transfer device according to the present invention is utilized.

In the following, preferred embodiments and a number of alternative embodiments of a fluid transfer device according to the invention will be described in greater detail with reference to the attached FIGS. 1-11.

The fluid transfer device 100, 200 according to the invention is intended for the in an infusion system and exhibits a first end 101, 201 and a second end 102, 202 opposite to the first end, wherein the second end 102, 202 is designed and arranged for coupling to an injection port 203, 203 of the infusion system 104, 204.

The fluid transfer device 100, 200 includes at least a first member 105, 205, a hollow needle 106, 206 attached to the first member, and a second member 107, 207 which is telescopically displaceable in relation to the first member 105, 205 in a way allowing the hollow needle 106, 206 to penetrate a flexible barrier member 108, 208 sealing the injection port 103, 203 in order to create a fluid passage from the first end 101, 201 via the injection port 203, 203 into the infusion system 104, 204.

According to the invention, the first end 101, 201 exhibits a connecting portion 109, 209, 309, 409 for attachment to a drug bottle 110, 210 containing a fixed dose D of a medical substance. The expression "fixed dose" should be understood as a predetermined quantity of the medical substance in question, which quantity has been adapted to the patient in question and which quantity is to be transferred in its entirety into the infusion system.

Furthermore, according to the invention, the second end 102, 202 exhibits a flexible membrane 213, 211 intended to be pressed against the flexible barrier member 108, 208 of the injection port 103, 203 with a pressure sufficient in order to create a double-membrane sealing 108, 111, 108, 211, 208, 211, around the hollow needle 105, 206 when creating the fluid passage into the infusion system 104, 204.

In a preferred embodiment of the fluid transfer device according to the invention, the flexible membrane 111, 211 is made of a polymer material exhibiting a yield point when subjected to the pressure, wherein the second end 102, 202 is designed and arranged for interacting with the injection port 103, 203. This ensures that a leakage-proof sealing can be achieved. Even more advantageously, the flexible membrane 111, 211 and the flexible barrier member 108, 208 are made of identical or similar materials which reach their yield points at the same pressure level.

Advantageously, the second end 102, 202 of the fluid transfer device is designed and arranged for creating the double-membrane sealing 108, 111, 108, 211 when the injection port 103 is provided on a flexible infusion bag 112 of the infusion system 104. Alternatively, the second end is designed and arranged for creating the double-membrane sealing when the injection port is provided on an infusion fluid line of the infusion system, or when the Injection port has been connected to a separate spike device SP exhibiting the flexible barrier member 208. Preferably, the second end is designed and arranged for all these cases.

In the preferred embodiment, the second end 102, 202 is designed and arranged for creating a double-membrane bayonet coupling with the injection port 103. Double-membrane bayonet couplings are known per se from the above-discussed '054 patent.

In a first, preferred embodiment of the invention, as illustrated in FIGS. 1-4 and 8, the connecting portion 109, 309 includes at least one locking member 113, 313 for grasping a bottle neck 114 of the drug bottle 110 in order to create a permanent attachment. The connecting portion 109, 309 further includes a hollow piercing member 115 for penetrating a bottle cap 116 of the drug bottle 110 in order to extend the fluid passage into the drug bottle. This embodiment is particularly useful for drug bottles/vials of the type illustrated in FIG. 6.

Figure 4:
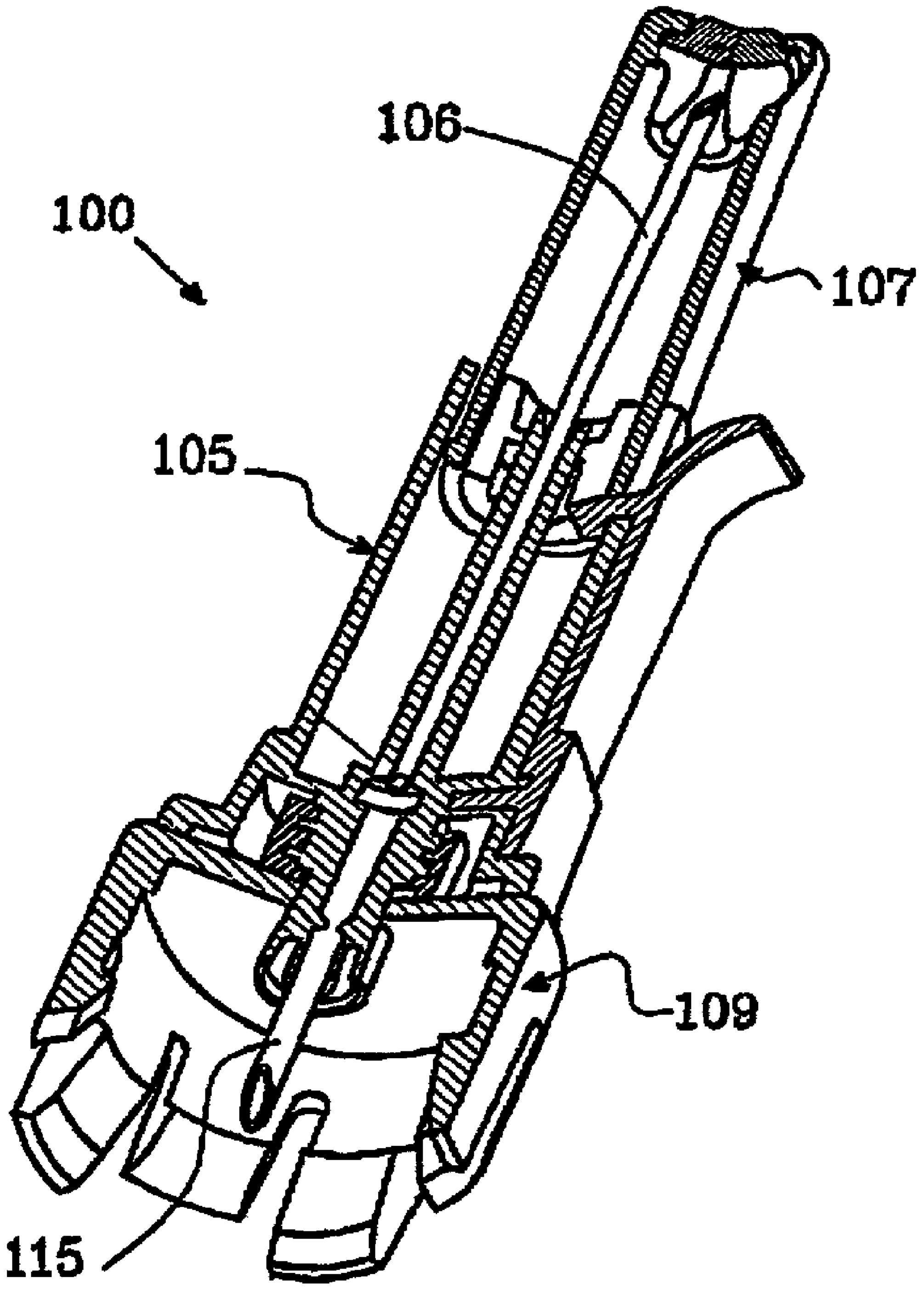
FIG. 4 shows the interior of the fluid transfer device in FIG. 2.

In the first embodiment of the invention as illustrated in FIG. 4, the connecting portion 109 exhibits a hollow piercing member 115 for penetrating a bottle cap 116 of the drug bottle 110 (see, FIG. 6) in order to extend the fluid passage into the drug bottle. In this embodiment as illustrated in FIG. 4, neighboring ends of the hollow piercing member 115 and the hollow needle 106 are designed and arranged in a way allowing fluid communication through the hollow piercing member 115 into the hollow needle 106.

In an alternative embodiment (not shown in the drawings), the connecting portion exhibits a hollow piercing member for penetrating a bottle cap of the drug bottle In order to extend the fluid passage into the drug bottle, wherein the hollow piercing member is constituted of a sharpened end of the hollow needle being exposed at the first end of the fluid transfer device. Accordingly, the components 106 and 115 in the embodiment shown in FIG. 4 could be replaced by a single hollow needle with two sharpened opposite ends.

Figure 5:
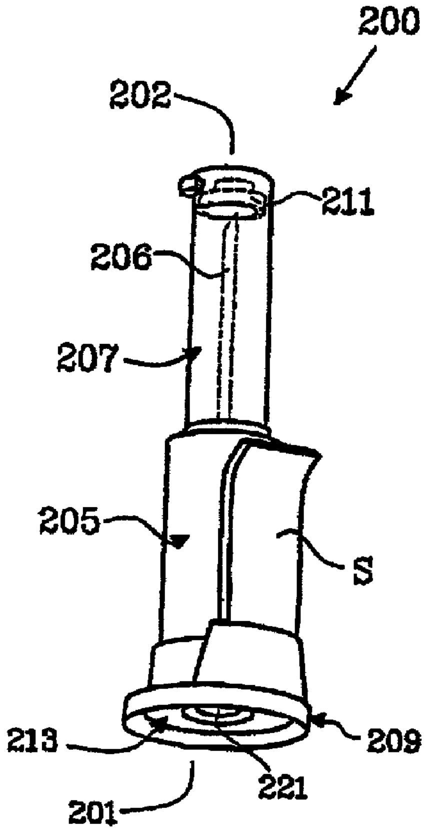
FIG. 5 is a schematic perspective view of a fluid transfer device according to a second embodiment of the invention.
Figure 7:
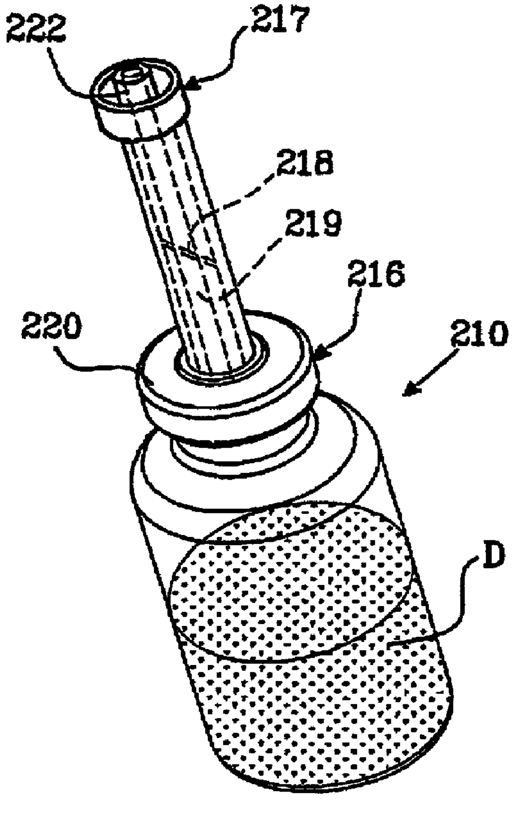
FIG. 7 shows a drug bottle according to a second embodiment of the invention, intended far use with the fluid transfer device in FIG. 5.

In a second embodiment of the fluid transfer device according to the invention, illustrated in FIGS. 5 and 7, the connecting portion 209 includes a first coupling member 213 for engaging a second coupling member 217 provided on a bottle cap 216 of the drug bottle 210, thereby creating an attachment by means of a Luer-lock coupling. Luer-lock couplings are well known per se, but for other uses.

In the second embodiment, the connecting portion 209 preferably includes a first coupling member 213 for attachment to a second coupling member 217 provided on a bottle cap 216 of the drug bottle 210. A fluid barrier member 218 is provided in a duct 219 extending between an interior D of the drug bottle 210 and the second coupling member 217. The fluid barrier member 218 can be ruptured by an external force in order to extend the fluid passage into the drug bottle 210. Accordingly, in the second embodiment, the breakable fluid barrier member 218 provides the function of the piercing member 115 penetrating the bottle cap 116 of the drug bottle in the first embodiment.

In the second embodiment, as illustrated in FIGS. 5 and 7, the connecting portion 209 advantageously includes a first coupling member 213 attachable to a second coupling member 217 permanently attached to the drug bottle 210, at least partly by means of an annular capsule member 220. However, it is also conceivable that the second coupling member is attached to the drug bottle in another suitable way.

In the second embodiment, the connecting portion preferably includes a female Luer-lock connector 221 for attachment to a male Luer-lock connector 222 provided on the drug bottle 210 or, alternatively, the connecting portion includes a male Luer-lock connector for attachment to a female Luer-lock connector provided on the drug bottle.

Figure 2:
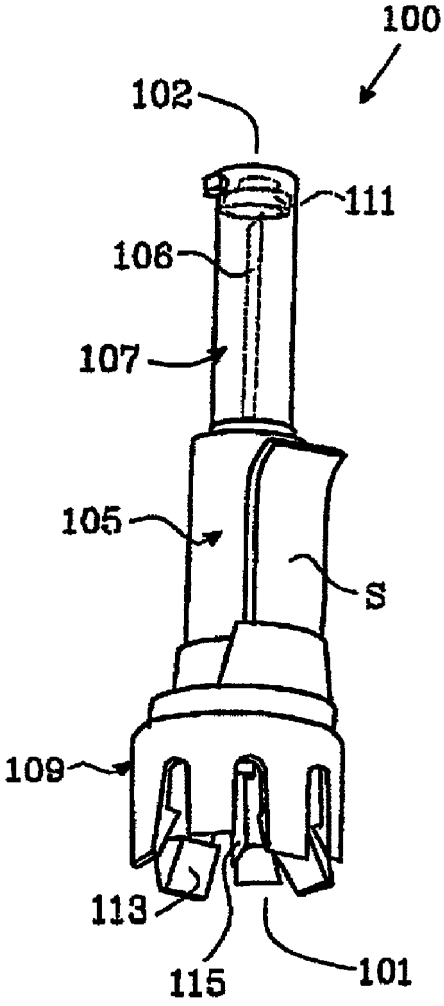
FIG. 2 is a schematic perspective view of a fluid transfer device according to a first, preferred embodiment of the invention.
Figure 3:
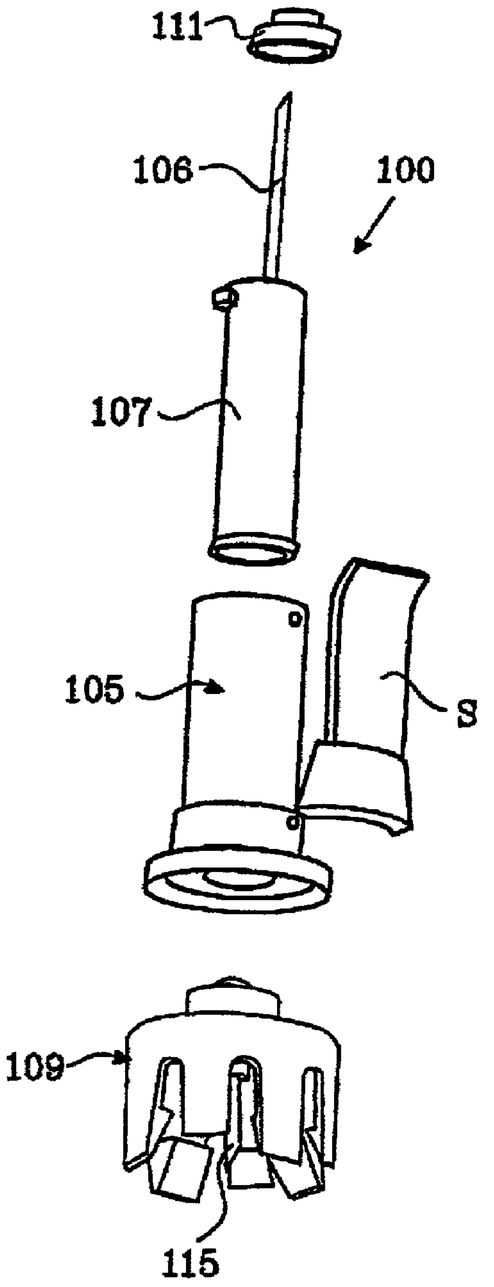
FIG. 3 is an exploded view of the fluid transfer device in FIG. 2.

In the first, preferred embodiment of the fluid transfer device according to the invention, as illustrated in FIGS. 2-4, the connecting portion is a separate component log which has been attached to the first member 105 before permanent attachment to the drug bottle 110.

In a particularly advantageous embodiment, the connecting portion is an integral part 209 of the first member 205, e.g., as illustrated in FIGS. 5 and 7. Alternatively, components 105 and 109 in FIG. 3 could be replaced by a single component instead.

Figure 8:
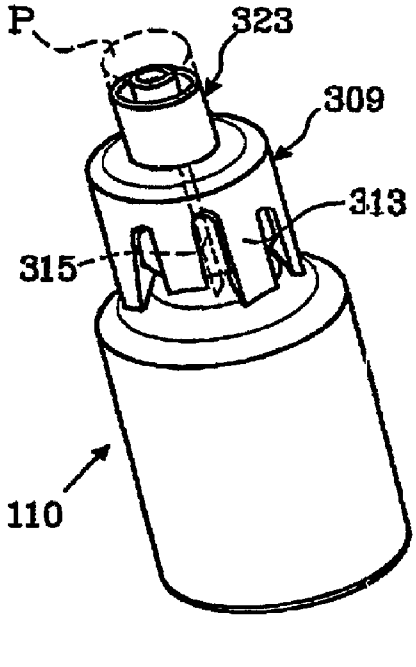
FIG. 8 shows the drug bottle in FIG. 6 permanently attached to a separate connecting portion which exhibits a Luer-lock connector for attachment to the fluid transfer device in FIG. 5 by means of a Luer-lock coupling.

In another alternative embodiment, as illustrated by FIGS. 5 and 8 together, the connecting portion is a separate component 309 having a Luer-lock connector 323 attachable to the first member 205 by means of a Luer-lock coupling 221, 323. This embodiment makes it possible to utilize the same type of fluid transfer device 200 with different drug bottles, e.g., the two types illustrated in FIGS. 8 and 7.

Figure 9:
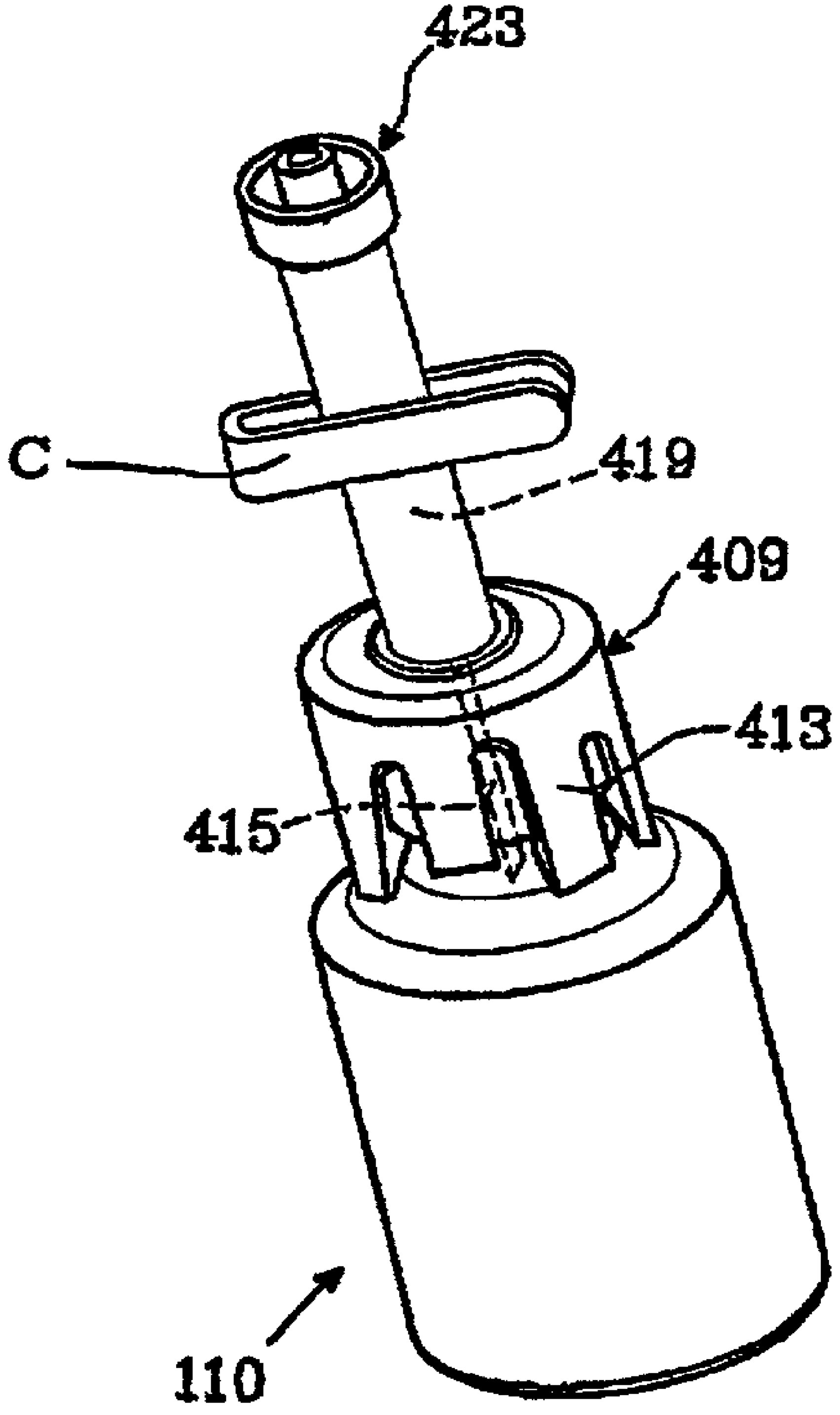
FIG. 9 shows the drug bottle in FIG. 6 permanently attached to a separate connecting portion of a fluid transfer device according to an alternative embodiment of the invention.
Figure 10:
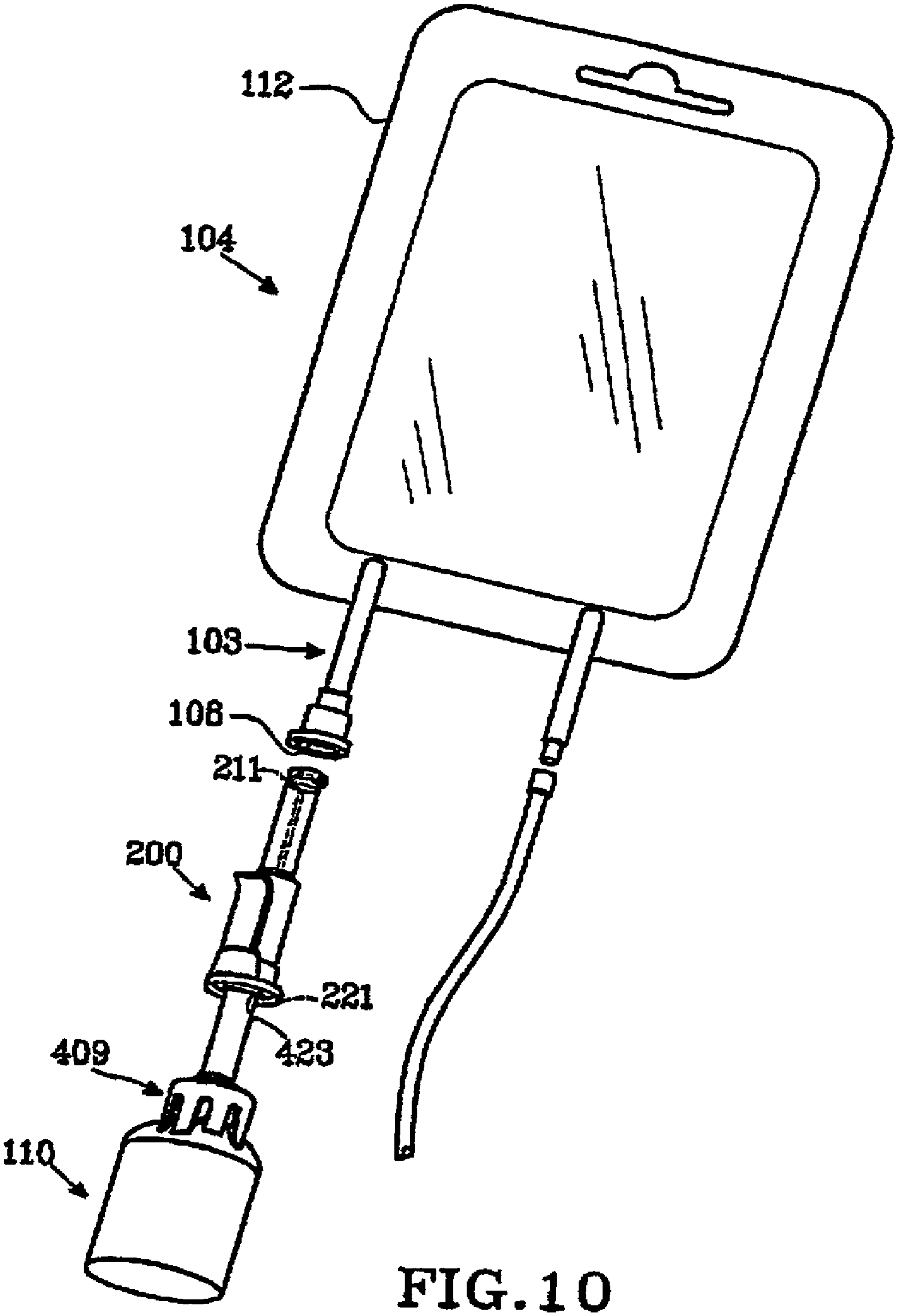
FIG. 10 is a schematic illustration of a portion of an infusion system in which a fluid transfer device according an alternative embodiment of the Invention is utilized.

In still another alternative embodiment, as illustrated in FIGS. 9 and 10 together, the connecting portion is a separate component 409 having a Luer-lock connector 423 attachable to the first member by means of a Luer-lock coupling 221, 423. In this embodiment, the connecting portion further exhibits at least one locking member 413 for grasping a bottle neck of the drug bottle 110 in order to create a permanent attachment, and a hollow piercing member 415 for penetrating a bottle cap of the drug bottle 110 in order to extend the fluid passage into the drug bottle.

In the following, a preferred embodiment and a number of alternative embodiments of a drug bottle according to the invention will be described with particular reference to FIGS. 6-9.

The drug bottle 110, 210 according to the invention contains a fixed dose D of a medical substance, wherein the drug bottle 110, 210 is intended for attachment to a fluid transfer device 100, 200 according to the invention.

Figure 6:
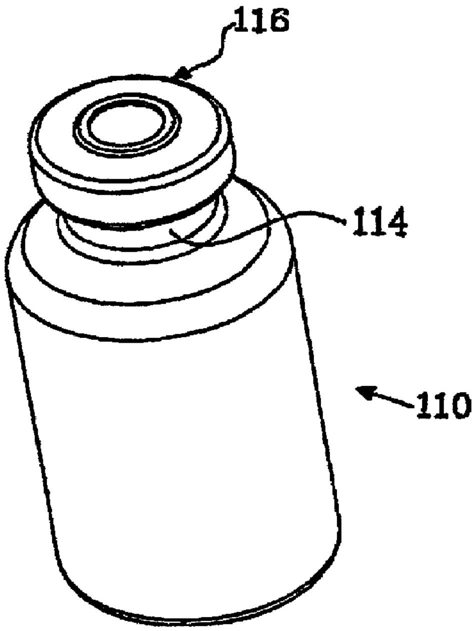
FIG. 6 shows a drug bottle according to a first embodiment of the invention, intended for use with the fluid transfer device in FIG. 2.

In a first advantageous embodiment, illustrated in FIG. 6, the drug bottle 110 includes a bottle neck 114 intended to be grasped by at least one locking member 113 of the connecting portion 109, thereby creating a permanent attachment. Preferably, as indicated in FIGS. 8 and 9, the drug bottle 110 includes a bottle cap 116 able to be pierced by a piercing member 115, 315 that is part of the fluid transfer device according to the invention.

In a second, preferred embodiment of the drug bottle according to the invention, illustrated in FIG. 7, the drug bottle 210 is sealed by a bottle cap 216 having a second coupling member 217 attachable to a first coupling member 213 of the connecting portion 209.

In a particularly preferred embodiment, as illustrated in FIG. 7, the drug bottle 210 is sealed by a bottle cap 226 having a second coupling member 217. A fluid barrier member 218 is provided in a duct 219 extending between an interior D of the drug bottle 210 and the second coupling member 214. The fluid barrier member 218 is able to be ruptured by means of an external force in order to open the duct 219. Breakable fluid barrier members are known per se for other uses, and can be designed in any suitable way and from any suitable material as long as the barrier is capable of performing the desired function.

As illustrated in FIG. 9, other embodiments are conceivable where the breakable fluid barrier member is replaced or assisted by a suitable damping member C. The damping member C further makes it possible to prevent undesired reflux of drug/infusion fluid into the drug bottle while this is connected to the infusion system. Such clamping members are known per se. Advantageously, as illustrated in FIG. 7, the drug bottle 210 is sealed by a bottle cap 216 having a second coupling member 217 attachable to a first coupling member 213 of the connecting portion 209. The second coupling member 217 is permanently attached to the drug bottle 210 at least partly by means of an annular capsule member 220. This embodiment makes it possible to utilize fairly conventional machinery for attaching such a specially designed bottle cap to a drug bottle or vial.

Most preferably, as illustrated in FIG. 7, the drug bottle 210 is sealed by a bottle cap 216 having a male Luer-lock connector 222 attachable to a female Luer-lock connector 221 of the connecting portion 209. Alternatively, the drug bottle is seated by a bottle cap having a female Luer-lock connector attachable to a male Luer-lock connector of the connecting portion.

Following, a preferred embodiment and number of alternative embodiments of a method for fluid transfer in an infusion system according to the invention will be described in greater detail with reference to the attached FIGS. 1-11.

The method includes using a fluid transfer device 100, 200 to inject a medical substance into the infusion system 104 via an injection port 103 sealed by a flexible barrier member 108. The fluid transfer device includes at least a first member 105, 205, a hollow needle 106, 206 attached to the first member, and a second member 107, 207 telescopically displaceable in relation to the first member 105, 205.

According to the invention, the method includes providing the fluid transfer device 100, 200 with a first end 101, 201, and a second, opposite end 102, 202 having a flexible membrane 111, 211, providing a drug bottle 110, 210 containing a fixed dose D of the medical substance, attaching the first end 101, 201 to the drug bottle 110, 210, and coupling the second end 101, 202 to the inspection port 103 while pressing the flexible membrane 111, 211 against the flexible barrier member 108 with a pressure sufficient for creating a double-membrane sealing 108, 111, 108, 211.

Furthermore, according to the invention, the method includes creating a fluid passage from the first end 101, 201 to the infusion system by means of telescopically displacing the first end 101, 201 in a direction towards the second end 202, 202 whereby the hollow needle 1 06, 206 penetrates the flexible membrane 111, 211 and the flexible barrier member 108 while being surrounded by the double-membrane sealing 108, 111, 108, 211, and transferring the fixed close D from the drug bottle 110, 210 into the infusion system 104 by means of creating and subsequently releasing a positive pressure inside the drug bottle 110, 210.

Advantageously, the injection port 103 is provided on a flexible infusion bag 112 of the infusion system 104. Alternatively, the injection port is provided on an infusion fluid line of the infusion system.

In a preferred embodiment of the method, the second end 102, 202 creates a double-membrane bayonet coupling with the injection port 103.

In a first embodiment according to the invention, the method further includes penetrating a bottle cap 116 of the drug bottle 110 by a hollow piercing member 115, 315 in order to extend the fluid passage into the drug bottle, and grasping a bottle neck 114 of the drug bottle 110 by at least one locking member 123 of the fluid transfer device 100, thereby creating a permanent attachment.

In an alternative embodiment of the method according to the invention, as illustrated by FIGS. 5 and 7, the attachment is created by means of a Luer-lock coupling 221, 222.

In another embodiment of the method according to the invention, as illustrated in FIG. 7, a fluid barrier member 218 blocking a duct 219 extending through the bottle cap 216 is ruptured by means of an external force when extending the fluid passage into the drug bottle 210.

In an alternative embodiment of the method, illustrated in FIG. 9, a clamping member C is utilized for applying an external pressure on a duct 419 extending through the bottle cap in order to block the fluid passage into the drug bottle. The use of such clamping members makes it possible to connect different components of an infusion system to each other without any risk of hazardous leakage to the environment also in embodiments where there are no breakable fluid barrier members or the like sealing the fluid containers of the infusion system.

Figure 11:
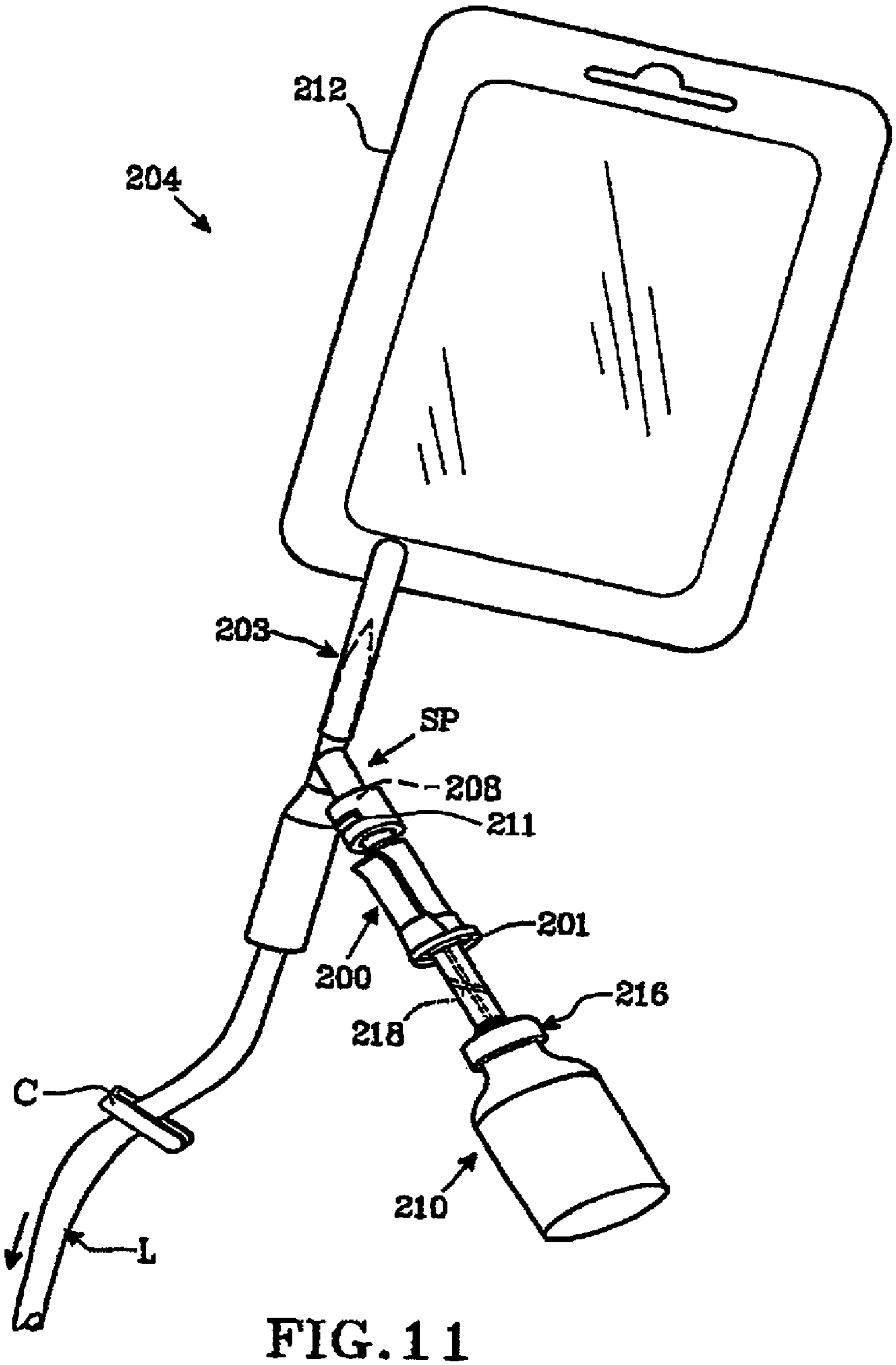
FIG. 11 shows the fluid transfer device of FIG. 5 and the drug bottle of FIG. 7 when coupled to a spike device of an alternative infusion system.

In still another alternative embodiment, illustrated in FIG. 11, the flexible membrane 211 of the second end is pressed against a flexible barrier member 208 of a spike device SP connected to the infusion system 204 before transferring the fixed dose from the drug bottle 210 into the infusion system 204. As illustrated in FIG. 11, a clamping member C is advantageously provided, thereby ensuring that the drug can be transferred from the drug bottle 210 into the infusion fluid container 212 and allowing mixing with the infusion fluid before initiating infusion through the infusion line L.

In another advantageous embodiment of the method according to the invention, schematically indicated in FIG. 8, the fluid transfer device includes at least one protective cap P which is removed before creating the fluid passage. If necessary, several protective caps, hoods, seals, or films can be provided on different portions of the fluid transfer device and the drug bottle according to the invention, and also on the injection port of the infusion system. This embodiment ensures that those surfaces of the fluid transfer system in contact with the infusion fluid and the supplied drug are kept in a sterile condition.

As illustrated in FIGS. 2-3 and 5, the fluid transfer device according to the invention can advantageously be provided with a safety latch S that controls the telescopic action of the first 105, 205 and second 107, 207 members.

As used herein, the expression "drug bottle" refers to any container that is leakage-proof and otherwise suitable for the purpose in question. Preferably, the "drug bottle" utilized in the assembly according to the invention has only one opening which is sealed by a closure or cap, and is preferably made of a solid, rigid and inflexible material, such as glass.

While there has been disclosed effective and efficient embodiments of the invention using specific terms, it should be well understood that the invention is not limited to such embodiments as there might be changes made in the arrangement, disposition, and form of the parts without departing from the principle of the present invention as comprehended within the scope of the accompanying claims.

The invention claimed is:

1. A fluid transfer device for temporarily establishing fluid communication between a drug bottle and an infusion fluid container that is adapted for transferring a medical substance from the drug bottle to the infusion fluid container for mixture with infusion fluid contained therein and the fluid transfer device is configured to prevent leakage of the medical substance into the ambient environment during both transfer of the medical substance into the infusion fluid container and after disconnect of the fluid transfer device from the infusion fluid container, said fluid transfer device comprising:

a first end including a connecting portion for interconnection with a drug bottle containing a fixed dose of a medical substance;

a second end opposite said first end and configured to be releasably coupled to an injection port of the infusion fluid container that is sealed by a pierceable flexible barrier, said second end of said transfer device having a flexible membrane located to be pressed against the flexible barrier of the injection port when coupled thereto; and a first member having a hollow needle attached thereto and said first member being telescopically associated with a second member so that upon displacement in a first direction of said first member relative to said second member when said fluid transfer device is coupled to the injection port, said hollow needle pierces said flexible membrane and the flexible baffler whereby creating a fluid passage from said first end into the infusion fluid container with whereby a double membrane seal is formed around said hollow needle by said flexible membrane and said flexible barrier of the injection port, and wherein said first member is arranged to be displaceable in a second opposite direction while said fluid transfer device is connected to said infusion fluid container and said drug bottle, to reverse said displacement relative to said second member.

2. The fluid transfer device according to claim 1, wherein said second end is configured to create said double-membrane seal around said hollow needle when the injection port is provided on a flexible infusion bag.

3. The fluid transfer device according to claim 1, wherein said second end is configured to create said double-membrane seal around said hollow needle when the injection port is provided on au infusion fluid line.

4. The fluid transfer device according to claim 1, wherein said second end is configured to create said double-membrane seal around said hollow needle when the injection port is connected to a spike device exhibiting the flexible barrier.

5. The fluid transfer device according to claim 1, wherein said second end is configured to create a double-membrane bayonet coupling with the injection port.

6. The fluid transfer device according to claim 1, said connecting portion comprising at least one locking member for grasping a bottle neck of the drug bottle in permanent attachment thereto, and said connecting portion further comprising a hollow piercing member for penetrating a bottle cap of the drug bottle and thereby extending said fluid passage into the drug bottle.

7. The fluid transfer device according to claim 1, said connecting portion comprising a hollow piercing member for penetrating a bottle cap of the drug bottle and thereby extending said fluid passage into the drug bottle, and wherein neighboring ends of said hollow piercing member and said hollow needle are configured to allow fluid communication through said hollow piercing member into said hollow needle.

8. The fluid transfer device according to claim 1, said connecting portion comprising a hollow piercing member for penetrating a bottle cap of the drug bottle and thereby extending said fluid passage into the drug bottle, said hollow piercing member comprising a sharpened end of said hollow needle exposed at said first end or said fluid transfer device.

9. The fluid transfer device according to claim 1, said connecting portion comprising a first coupling member engageable with a second coupling member provided on a bottle cap of the drug bottle and thereby establishing a luer-lock coupling.

10. The fluid transfer device according to claim 1, further comprising:

said connecting portion comprising a first coupling portion member configured for attachment to a second coupling member provided on a bottle cap of the drug bottle; and a fluid baffler member provided in a duct extending between an interior of the drug bottle and said second coupling member, said fluid barrier member ruptureable by means of an external force which extends said fluid passage into the drug bottle.

11. The fluid transfer device according to claim 1, said connecting portion comprising a first coupling member attachable to a second coupling member whereby said second coupling member is permanently attached to the drug bottle utilizing an annular capsule member.

12. The fluid transfer device according to claim 1, said connecting portion comprising a female Luer-lock connector attachable to a male Luer-lock connector provided on the drug bottle.

13. The fluid transfer device according to claim 1, said connecting portion comprising a male Luer-lock connector attachable to a female Luer-lock connector provided on the drug bottle.

14. The fluid transfer device according to claim 1, wherein said connecting portion is a separate component attached to said first member before permanent attachment to the drug bottle.

15. The fluid transfer device according to claim 1, wherein said connecting portion is an integral part of the first member.

16. The fluid transfer device according to claim 1, wherein said connecting portion is a separate component comprising a Luer-lock connector attachable to said first member by means of a Luer-lock coupling.

17. The fluid transfer device according to claim 1, wherein said connecting portion is a separate component comprising:

a Luer-lock connector attachable to said first member by means of a Luer-lock coupling;

at least one locking member capable of grasping a bottle neck of the drug bottle and thereby creating a permanent attachment; and a hollow piercing member capable of penetrating a bottle cap of the drug bottle and thereby extending said fluid passage into the drug bottle.

18. The fluid transfer device according to claim 1, further comprising the drug bottle which contains a fixed dose of a medical substance and which is configured to be attached to the fluid transfer device.

19. The fluid transfer device according to claim 18, said drug bottle further comprising a bottle neck graspable by at least one locking member of said connecting portion and thereby creating a permanent attachment.

20. The fluid transfer device according to claim 18, said drug bottle further comprising a bottle cap pierceable by a piercing member of said fluid transfer device.

21. The fluid transfer device according to claim 18, said drug bottle further comprising a bottle cap for sealing the drug bottle, the bottle cap comprising a second coupling member attachable to a first coupling member of said connecting portion.

22. The fluid transfer device according to claim 18, further comprising a bottle cap sealing said. drug bottle, said bottle cap comprising a second coupling member, wherein a fluid barrier member is provided in a duct extending between an interior of said drug bottle and said second coupling member, said fluid baffler member rupturable by means of an external force that opens said duct.

23. The fluid transfer device according to claim 18, further comprising a bottle cap for sealing said drug bottle, said bottle cap comprising a second coupling member attachable to a first coupling member of said connecting portion, wherein said second coupling member is permanently attached to said drug bottle at least partly by means of an annular capsule member.

24. The fluid transfer device according to claim 18, further comprising a bottle cap for sealing said drug bottle, said bottle cap comprising a male Luer-lock connector able to be attached to a female Luer-lock connector of said connecting portion.

25. The fluid transfer device according to claim 18, further comprising a bottle cap for sealing said drug bottle, said bottle cap comprising a female Luer-lock connector attachable to a male Luer-lock connector of said connecting portion.

26. A method for fluid transfer in an infusion system, said method comprising:

utilizing a fluid transfer device to inject a medical substance from a drug bottle containing a fixed dose of said medical substance into an infusion system via an injection port sealed by a flexible barrier member, said fluid transfer device comprising at least a first member, a hollow needle attached to said first member, and a second member telescopically and retractably displaceable in relation to said first member, said fluid transfer device further comprising a first end, and a second, opposite end having a flexible membrane;

attaching said first end of said fluid transfer device to said drug bottle;

releasably coupling said second end of said fluid transfer device to said injection port while pressing said flexible membrane against said flexible barrier member with a pressure sufficient for creating a double-membrane sealing by said flexible membrane and said flexible barrier member;

creating a fluid passage from said first end of said infusion system by telescopically displacing said first end in a direction towards said second end and thereby allowing said hollow needle to penetrate said flexible membrane and said flexible barrier member while being surrounded by said double-membrane sealing formed by said flexible membrane and flexible barrier membrane;

transferring said fixed dose from said drug bottle into said infusion system by means of creating and subsequently releasing a positive pressure inside said drug bottle; and displacing said first end away from said second end while said fluid transfer device is connected to said infusion system and said drug bottle.

27. The method for fluid transfer according to claim 26, wherein said injection port is provided on a flexible infusion bag of said infusion system.

28. The method for fluid transfer according to claim 26, wherein said injection port is provided on an infusion fluid line of said infusion system.

29. The method for fluid transfer according to claim 26, further comprising:

creating a double-membrane bayonet coupling between the second end and said injection port.

30. The method for fluid transfer according to claim 26, further comprising:

penetrating a bottle cap of said drug bottle by means of a hollow piercing member in order to extend said fluid passage into said drug bottle; and grasping a bottle neck of said drug bottle by means of at least one locking member of said fluid transfer device and thereby creating a permanent attachment.

31. The method for fluid transfer according to claim 26, further comprising:

creating the attachments by a Luer-lock coupling.

32. The method for fluid transfer according to claim 26, further comprising:

rupturing a fluid barrier member blocking a duct extending through said bottle cap by an external force when extending said fluid passage into said drug bottle.

33. The method for fluid transfer according to claim 26, further comprising:

utilizing a clamping member for applying an external pressure on a duct extending through said bottle cap and thereby blocking said fluid passage into said drug bottle.

34. The method for fluid transfer according to claim 26, further comprising:

pressing the flexible membrane of said second end against a flexible baffler member of a splice device connected to said infusion system before transferring said fixed dose from said drug bottle into said infusion system.

35. The method for fluid transfer according to claim 26, further comprising:

providing the fluid transfer device with at least one protective cap, and removing the protective cap before creating said fluid passage.

36. A fluid transfer device for temporarily establishing fluid communication between a drug bottle and an infusion fluid container that is adapted for transferring a medical substance from the drug bottle to the infusion fluid container for mixture with infusion fluid container therein and the fluid transfer device is configured to prevent leakage of the medical substance into the ambient environment during both transfer of the medical substance into the infusion fluid container and after disconnect of the fluid transfer device from the infusion fluid container, said fluid transfer device comprising:

a first end including a connecting portion for interconnection with a drug bottle containing a fixed dose of a medical substance;

a second end opposite said first end and configured to be releasably coupled to an injection port of an infusion fluid container that is sealed by a pierceable flexible barrier, said second end of said transfer device having a flexible membrane located to be pressed against the flexible barrier of the injection port when coupled thereto; and a first member having a hollow needle attached thereto and said first member being telescopically associated with a second member, said first member and second member being displaceable relative to each other to and fro between two end positions, so that upon displacement of said first member in a first direction relative to said second member when said fluid transfer device is coupled to the injection port, said hollow needle pierces said flexible membrane and the flexible barrier thereby creating a fluid passage from said first end into the infusion fluid container with a double-membrane seal around said hollow needle, and upon displacement of said first member relative to said second member in a second direction opposite to the first direction, said hollow needle is withdrawn to a position within said flexible membrane while said fluid transfer device is connected to said infusion fluid container and said drug bottle, thereby enabling disconnection of the fluid transfer device from the infusion fluid container.

* * * * *

UNITED STATES PATENT AND TRADEMARK OFFICE

CERTIFICATE OF CORRECTION

PATENT NO. : 7,867,215 B2
APPLICATION NO. : 10/063386
DATED : January 11, 2011
INVENTOR(S) : Akerlund et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 869 days.

Signed and Sealed this
Twenty-seventh Day of September, 2011

David J. Kappos
*Director of the United States Patent and Trademark Office*

UNITED STATES PATENT AND TRADEMARK OFFICE

CERTIFICATE OF CORRECTION

PATENT NO. : 7,867,215 B2
APPLICATION NO. : 10/063386
DATED : January 11, 2011
INVENTOR(S) : Roger Akerlund It is certified that error appears in the above-identified patent and that said Letters Patent is hereby corrected as shown below:

Title Page, Item [73] Assignee, please delete “Gothenburg, (SE)” and insert --Göteborg, (SE)-- therefor;

Column 9, line 11 (Claim 1), please delete “baffler” and insert --barrier-- therefor;

Column 9, line 28 (Claim 3), please delete “au” and insert --an-- therefor;

Column 9, line 66 (Claim 10), please delete “baffler” and insert --barrier-- therefor;

Column 10, line 55 (Claim 22), please delete “said.” and insert --said-- therefor;

Column 10, line 59 (Claim 22), please delete “baffler” and insert --barrier-- therefor;

Column 12, line 14 (Claim 34), please delete “baffler” and insert --barrier-- therefor.

Signed and Sealed this
Twenty-fifth Day of October, 2011

David J. Kappos

David J. Kappos
*Director of the United States Patent and Trademark Office*